United States Patent [19]
Raptis

[11] Patent Number: 6,001,617
[45] Date of Patent: Dec. 14, 1999

[54] ELECTROPORATION DEVICE AND METHOD OF USE

[75] Inventor: Leda Raptis, Kingston, Canada

[73] Assignee: Queen's University at Kingston, Kingston, Canada

[21] Appl. No.: 07/531,671

[22] Filed: Jun. 1, 1990

[30] Foreign Application Priority Data

Jun. 7, 1989 [CA] Canada ..................................... 602075

[51] Int. Cl.$^6$ ............................ C12N 13/00; C12M 3/00; C12M 3/04; C12M 1/22; C25B 7/00; B01D 61/42
[52] U.S. Cl. ........................ 435/173.1; 435/284; 435/285; 435/297; 435/817; 204/180.1; 204/299 R
[58] Field of Search ................................ 435/173.1, 284, 435/285, 297, 817; 204/180.1, 299 R

[56] References Cited

U.S. PATENT DOCUMENTS

| | | | |
|---|---|---|---|
| 4,441,972 | 4/1984 | Pohl | 204/183.1 |
| 4,804,450 | 2/1989 | Mochizuki et al. | 204/299 R |
| 4,832,814 | 5/1989 | Root | 435/287 |

OTHER PUBLICATIONS

Yaoita et al., Bioelectrochemistry and Bioenergetics 20, pp. 169–177, 1988.
Haacke, Ann. Rev. Mater. Sci., 7, pp. 73–93, 1977.
Hofmann et al. (1986) *IEEE Eng. Med. Biol,* Dec. pp. 6–23.

*Primary Examiner*—Douglas W. Robinson
*Assistant Examiner*—Jon P. Weber
*Attorney, Agent, or Firm*—Richard J. Hicks

[57] ABSTRACT

A method and apparatus for cell culture wherein cultured cells adhere and divide, in a monolayer, on an optically transparent planar electrode in the culture vessel. An electric current is applied between the planar electrode and a counter electrode so as to create an electric field between the electrodes which influences the characteristics of the cells growing thereon. In a preferred embodiment the planar electrode may be an optically transparent conducting layer coated onto the culture vessel bottom or the culture vessel may be made of an optically transparent electrically conducting material. The apparatus is particularly useful for the introduction of different biologically important molecules into cells or for cell fusion.

13 Claims, 1 Drawing Sheet

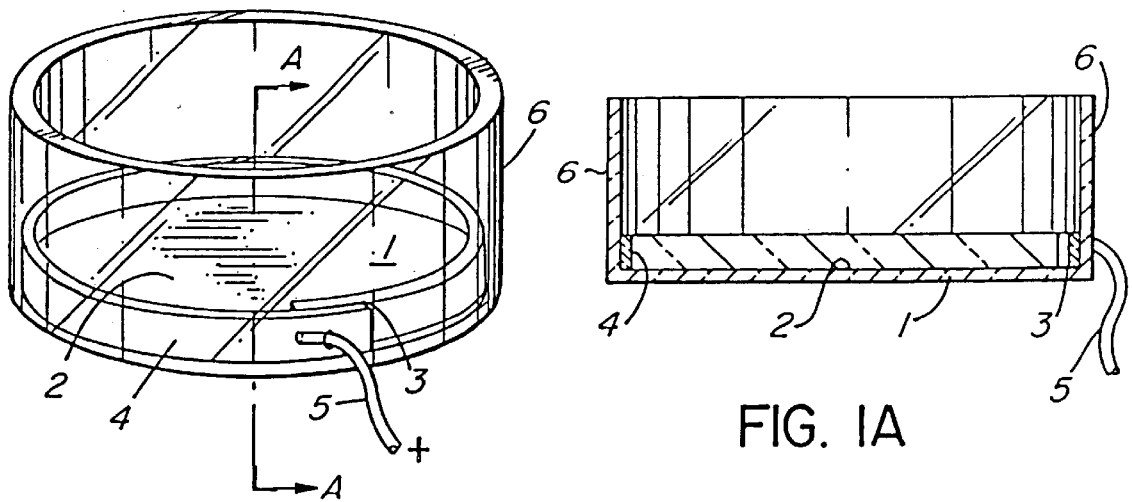
FIG. 1
FIG. 1A
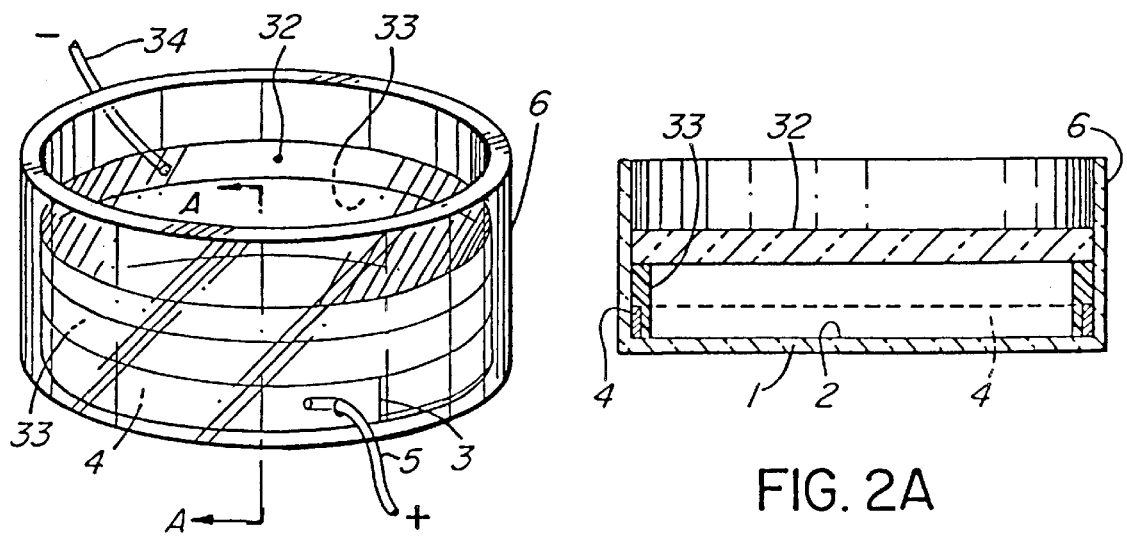
FIG. 2
FIG. 2A

ELECTROPORATION DEVICE AND METHOD OF USE

FIELD OF INVENTION

This invention relates to a cell culture assembly in which a monolayer of cells to be cultured adhere to the bottom thereof while they are treated with an electric current.

BACKGROUND OF INVENTION

Petri dishes have been used for cell culture for many years. They are generally circular transparent glass or plastic dishes having a substantially flat bottom and a relatively low (in relation to the diameter of the dish) side wall. Glass and most plastics are, however, non-conducting and generally it is not possible to subject cells growing in a Petri dish to an electric field of any significant intensity. It is known that most cells, when subjected to an electric field undergo changes in their cell wall structure with the formation of holes through which a foreign gene, in the form of DNA or RNA, or other non-permeant molecule such as protein nucleotides or drugs, may be inserted, in a process which is known as electroporation.

For the introduction of DNA, electroporation has mostly been used for cells which cannot be easily transfected by the classical Graham and Van der Eb (1973) calcium technique, such as lymphocytes and bone marrow stem cells, which do not adhere to solid supports. Consequently, current electroporation techniques call for cells to be in suspension in a medium containing the DNA when the electric field is applied. Attention is directed to Canadian Patent 1,208,146 dated Jul. 22, 1986 to Wong. Attention has now turned, however, to the use and study of cells which do adhere to a solid substrate and which only grow when so adhering. Attempts to produce a suspension of such cells using a proteolytic enzyme, such as trypsin, substantially alters the cell membrane, the main barrier to DNA entry, and interferes with cell viability and reproducobility.

OBJECTS OF INVENTION

It is, therefore, an object of the present invention to provide an apparatus in which adherent cells can grow and be subjected to an electric field, in situ, so that the process of electroporation can be carried out.

Another object of the present invention is to provide an alternative electroporation method for adherent cells.

BRIEF STATEMENT OF INVENTION

By one aspect of this invention there is provided a cell culture device comprising:
a container to receive a selected cellular material and liquid growth media therefor;
said container including an optically transparent, electrically conductive planar substrate to which said cells may adhere and means in electrical contact with said substrate for applying an electric current to said substrate.

In a preferred aspect of the invention the aforesaid container is a petri dish having a planar, optically transparent, electrically conducting bottom selected from an electrically conducting polymeric material, and an optically transparent non-conductive material coated with an optically transparent electrically conductive material.

By another aspect of this invention there is provided a method for culturing cells which comprises:
providing a container having an optically transparent electrically conductive planar substrate upon which cells to be cultured adhere;
placing said cells and a growth medium therefor in said container and forming an adherent monolayer of said cells on said substrate, and subjecting said monolayer of cells to an electric current.

BRIEF DESCRIPTION OF DRAWINGS

FIG. 1 is a perspective view of a cultivation dish according to one embodiment of the present invention.

FIG. 1A is a cross section of the dish of FIG. 1 along line A—A.

FIG. 2 is a perspective view of a cultivation dish including the counter electrode.

FIG. 2A is a cross section of the dish of FIG. 2 along line A—A.

In FIG. 1 there is shown a planar electrode cell cultivation dish having a base or substrate 1 in the form of a circular disc of optically transparent material such as borosilicate glass sold under the tradename Pyrex (Corning Glass Co.) or a thermoplastic material such as polystyrene surrounded by a glass or plastic circumferential wall 6. The substrate 1 is coated with an electrically conducting, optically transparent coating 2, preferably 0.1 to about 5 microns thick. The coating material may be any material which offers the required properties of transparency, conductivity, chemical stability, and biological inertness, while encouraging cell adhesion of the cells to be cultured. Several advanced ceramic and semi conductor materials such as tin oxide, indium oxide, cadmium oxide, zinc oxide and mixtures thereof and certain doped oxides. Conductive plastic coatings may also be employed, such as "Velostat", a proprietary electrically conductive plastic for static protection marketed by the 3M Company, Minnesota. Any conventional method of depositing the coating may be employed including pyrolytic deposition, sol-gel processing, radio frequency or d.c. reactive sputtering, solvent dipping and curing, depending on the film material selected and the precise surface properties desired for a particular application. The thickness of the coating depends on the material employed and the desired application. Thicker coatings tend to have better conductivity but generally poorer light transmission properties. In some instances it may be desirable to precoat the substrate with a thin transparent layer of a noble metal such as gold or platinum in order to reduce the in-plane electrical resistance of the coating film.

A distribution electrode 4, in the form of a thin annular wire or strip surrounds the substrate 1, in electrical contact with coating 2. The electrode 4 is fabricated in any convenient conductive material such as copper, tin, platinum, silver or alloys thereof. The electrode 4 encircles the substrate 1 and the two ends thereof are bonded together at 3. A lead in wire 5 passes through the wall 6 and is attached to electrode 4. Wire 5 may be connected to an electric power source so that coating 2 is positively charged. The cells to be cultured are contained in cultivation dish, shown in FIG. 1. If they are adherent cells (like mammalian fibroblast or epithelial cells) they attach to the conductive surface (1,2) and grow. Non-adherent cells (such as cells the hemopoetic system or bacteria) can also be treated in the same chambers. If it is desired merely to permeate or to fuse cells an alternating electric current may be used. The electric field strength may be of the order of 100–8,000 V/cm for a few nanoseconds up to 1 second depending on the cells and the electroporation medium.

It will, of course, be appreciated that the Petri dish, or at least the planar bottom thereof, may be fabricated entirely from a conducting plastic material such as the one described above, in which case it is unnecessary to provide a conducting coating 2, as the entire base is conducting. In an alternative embodiment the transparent planar substrate may be provided within the Petri dish or other container and not necessarily in contact with the bottom thereof. Preferably such substrate is a porous substrate suspended within the container, to which the cells may adhere.

As noted, the cells grow, in a medium such as DMEM (Dulbeco's modification of Eagle's medium), on a conductive coating or conducting planar substrate 2 in a single or several layers which may be about 10–1,000 microns thick. In order to prevent crushing of the cells by the superimposed planar negatively charged, optically transparent, counter-electrode 32 (FIG. 2), and provided with a lead-in wire 34, there may be provided a non conducting annular ring 33, to about 1000 microns thick. Ring 33 is made from a material to which the cells do not adhere, in order to prevent short-circuiting, such as polytetrafluorethylene (Teflon®).

It will be appreciated by those skilled in the art that the apparatus as described herein is useful for electroporation in a conventional manner and in addition to electroporation may also be used for the introduction of a large variety of substances for different purposes. The device of the present invention is readily adapted to use for electrofusion of cells.

Other uses will also be apparent to those skilled in the art, including use in studies of cell behaviour under stimulation by an electric field.

It will also be appreciated that the efficiency of gene expression, in the case of introduction of DNA is much improved, since (1) the cells are not detached from the monolayer, therefore they are electroporated while they are in their optimal condition for growth and (2) the cells expose a much larger surface to the solution containing the DNA or other molecules to be introduced.

Besides, since the cell division cycle is not disrupted, the apparatus offers the possibility to study the cell cycle itself, which is impossible with the current electroporation methods. Moreover, the efficiency of introduction might be optimized by electroporating synchronized cells at distinct stages of their division cycle, notably the S (DNA synthetic phase) or mitosis, for the purpose of more efficient gene expression. Finally, the reproducibility of introduction should be much improved, since the cell membrane is not altered through trypsinization or other method of detachment from the monolayer.

I claim:

1. A cell culture device comprising:
   a container to receive selected cells and a growth media therefor and permit growth of selected cells; said container including an optically transparent, electrically conducting planar substrate to which a monolayer of said cells may adhere;
   optically transparent planar electrode means superimposed over said planar substrate but spaced therefrom; and means connected to said substrate and said electrode means so as to provide a potential gradient therebetween whereby an electrode field strength of between 1000 and 8000 volts per cm is generated and a substantially uniform electric current may be applied to said monolayer of adherent cells.

2. A cell culture device as claimed in claim 1 wherein said optically transparent substrate comprises an optically transparent base of a Petri dish forming said container.

3. A cell culture device as claimed in claim 2 wherein said substrate comprises an electrically conducting optically transparent polymeric material forming the base of said Petri dish.

4. A cell culture device as claimed in claim 2 wherein said substrate comprises an optically transparent, electrically conducting coating on said base.

5. A cell culture device as claimed in claim 4 wherein said coating is formed of tin oxide.

6. A cell culture device as claimed in claim 4 wherein said coating is formed of doped tin oxide, indium oxide, doped indium oxide, cadmium oxide, cadmium stannate, zinc oxide, zinc cadmium sulfite or titanium nitride.

7. A cell culture device as claimed in claim 1 including non-conductive spacer means between said planar electrode and said planar substrate.

8. A method for culturing cells which comprises:
   providing a container having an optically transparent electrically conductive planar substrate upon which cells to be cultured adhere, and a superimposed optically transparent planar electrode over said planar substrate but spaced therefrom;
   placing said cells and a growth medium therefor in said container and forming an adherent layer of said cells on said substrate; and
   providing a potential gradient between said planar electrode and said substrate so as to generate an electrode field strength of between 1000 and 8000 volts per cm between said planar electrode and said planar substrate and subject said adherent cells to an electric current for a selected period of time in the range of a nanosecond up to about one second.

9. A method as claimed in claim 8 wherein said cells are selected from eukaryotic cells and prokaryotic cells.

10. A method as claimed in claim 9 wherein said cells are mammalian cells.

11. A method as claimed in claim 8 wherein said adherent layer is a monolayer of said cells.

12. A method as claimed in claim 9 wherein said planar substrate is not in direct contact with said container.

13. Apparatus for subjecting in situ adherent cells to an electrical field of sufficient intensity to induce electroporation of in situ adherent cells while said cells are adhered to an electrode surface, said apparatus comprising:
   an electrically conductive surface conducive to cell adhesion and growth wherein said electrically conductive surface is disposed on at least one layer of material of greater conductivity;
   a counter-electrode;
   means for supporting said counter-electrode in contact with said medium and at a close distance from said surface; and
   means for applying an electric potential or electrical ionizing source to said surface and said counter-electrode.

* * * * *